United States Patent [19]

Lemelson

[11] Patent Number: 4,674,480
[45] Date of Patent: Jun. 23, 1987

[54] DRUG COMPOSITIONS AND METHODS OF APPLYING SAME

[76] Inventor: Jerome H. Lemelson, 85 Rector St., Metuchen, N.J. 08840

[21] Appl. No.: 631,605

[22] Filed: Jul. 17, 1984

Related U.S. Application Data

[63] Continuation-in-part of Ser. No. 614,038, May 23, 1984, and Ser. No. 614,021, May 25, 1984.

[51] Int. Cl.⁴ .............................................. A61K 49/02
[52] U.S. Cl. ...................................... 128/1.1; 128/659; 264/4.1; 264/4.32; 424/1.1; 424/9; 424/19; 424/490; 428/402.2
[58] Field of Search ........................ 424/1.1, 9, 19, 22; 264/4.1, 4.32; 428/402.2; 128/1.1, 659

[56] References Cited

U.S. PATENT DOCUMENTS

| | | | |
|---|---|---|---|
| 3,179,600 | 4/1965 | Brockett | 428/402.2 |
| 4,209,700 | 6/1980 | Stoddart | 250/363 S |
| 4,310,505 | 1/1982 | Baldeschwieler et al. | 424/1.1 |
| 4,310,506 | 1/1982 | Baldeschwieler et al. | 424/1.1 |
| 4,311,688 | 1/1982 | Burchlec et al. | 424/1.1 |
| 4,323,546 | 4/1982 | Crockford et al. | 424/1.1 |
| 4,331,647 | 5/1982 | Goldenberg | 424/1.1 |
| 4,334,017 | 6/1982 | Plotkin et al. | 435/7 |
| 4,348,376 | 9/1982 | Goldenberg | 424/1.1 |
| 4,361,544 | 11/1982 | Goldenberg | 424/1.1 |
| 4,429,008 | 1/1984 | Martin et al. | 424/1.1 |
| 4,434,153 | 2/1984 | Urquhart et al. | 424/22 |
| 4,444,744 | 4/1984 | Goldenberg | 424/1.1 |
| 4,448,765 | 5/1984 | Ash et al. | 424/1.1 |
| 4,460,559 | 7/1984 | Goldenberg | 424/1.1 |
| 4,460,560 | 7/1984 | Tökes et al. | 424/1.1 |
| 4,460,561 | 7/1984 | Goldenberg | 424/1.1 |
| 4,466,951 | 8/1984 | Pittman | 424/1.1 |

OTHER PUBLICATIONS

Gregoriadis et al., Bio. Chem. Biophys. Res. Comm., vol. 65 (1975) 537–544.

Primary Examiner—Christine M. Nucker

[57] ABSTRACT

A composition and method for targeting and applying drugs or medication to a select location or locations within a living being. Drug units are produced, each of which is formed of at least one antibody, such as a monoclonal antibody, a small quantity of a medication such as a chemical or organic material and a small quantity of a nuclide which is normally inactive but which may be rendered explosively radioactive when targeted within a living body by external radiation passed through the body to the drug unit. When so rendered radioactive, the medication is released to infiltrate or be absorbed by surrounding tissue. In a particular form, the system also includes means for detecting the location or locations of concentrations of such drug units within the body and controlling the generation and direction of activating radiation passed through the body from an external source to cause the nuclide material existing in each drug unit to become radioactive and, in so doing, to effect the controlled or immediate release of medication from the drug unit. In yet another form, drug units are formed of microcapsules, such as microballoons made of biodegradable material containing one or more medications, biological elements or diagnostic material such as a dye or radioactive tracing chemical, releasable from encapsulation after the drug units have become targeted to specific antigenic material when the encapsulation material biodegrades under the action of body fluid.

28 Claims, 8 Drawing Figures

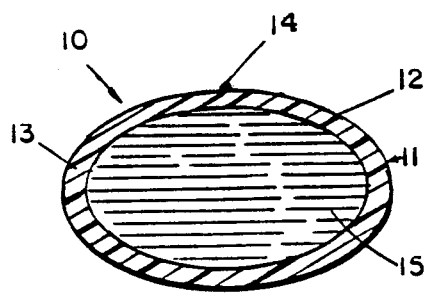
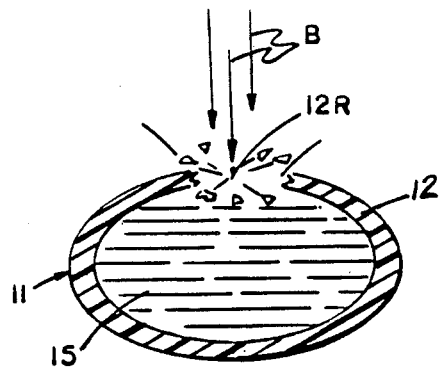
FIG.1　　　　　　FIG.2
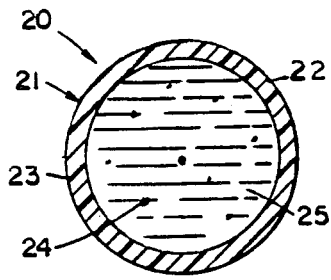
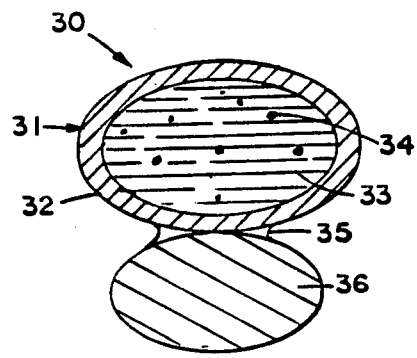
FIG.3　　　　　　FIG.4
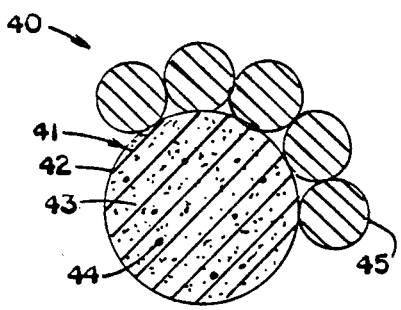
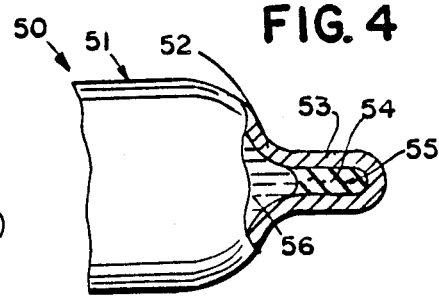
FIG.5　　　　　　FIG.6
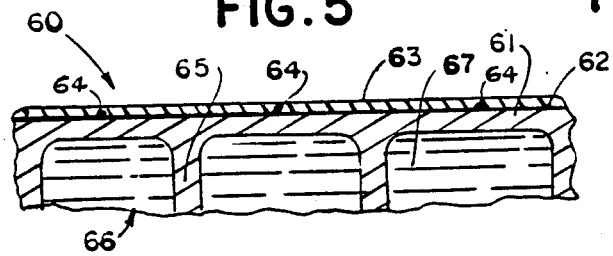
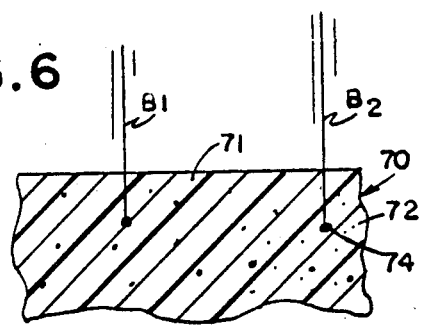
FIG.7　　　　　　FIG.8

DRUG COMPOSITIONS AND METHODS OF APPLYING SAME

RELATED APPLICATIONS

This is a continuation-in-part of copending applications Ser. Nos. 614,038 filed May 23, 1984 and 614,021 filed May 25, 1984, respectively entitled "Compositions of Matter for Use in Medical Treatment" and "Medical Scanning, Monitoring and Treatment System and Method".

BACKGROUND OF THE INVENTION

This invention relates to a system and method for controlling the flow or release of a fluid from a container or containers thereof, such as a capsule or reservoir disposed within tissue or a body cavity of a living being. In particular, the invention relates to a system and method which operates under controlled radiation generated outside the body of a living being and directed to the skin and tissue thereof to generate either a local, controlled miniature explosion to effect such fluid release action. The fluid may comprise a drug or other material useful in the treatment and/or diagnosis of a human malady, wherein it is desired to effect the controlled release of such fluid without directly connecting wires or one or more conduits for a fluid to an actuation means by extending same to the tissue of the body.

In my co-pending patent application Ser. No. 614,038 I disclose the drug units which may be targeted to a specific antigen or antigens located within a living body using antibodies. At least one of the antibodies forms part of each drug unit and is targeted to dispose and retain the drug unit at a specific location, such as within or adjacent to a tumor or malignancy. The cells of the tumor contain antigens to which the antibodies of the drug units become attached. When so located, the drug units may be used (1) to detect the location and extent of the antigenic material or diseased cells and (2) to effect treatment of the disease when small quantities of nuclide material, such as Boron 10, are activated with externally applied radiation, such as neutrons, passed through the body to the site or sites or such drug units.

Accordingly, it is a primary object of this invention to provide a new and improved composition and method for employing drugs and medication in the treatment of maladies of living beings.

Another object is to provide a new and improved composition and method for delivering drugs to a selected site or sites in a living being.

Another object is to provide a composition and method for delivering one or more selected drugs to one or more diseased sites in a living being and releasing such drug or drugs from retaining means or containers at such site or sites.

Another object is to provide a composition and method for targeting encapsulated drugs to select diseased tissue, such as a tumor or tumors, within a living being and controllably releasing such drugs when so targeted.

Another object is to provide an improved composition and method for delivering precise quantities of medication or drug units to select diseased tissue, such as tumors and organs within a living being and controllably effecting the release of such medication thereat for controlled treatment purposes.

Another object is to provide new and improved compositions of matter for use in the controlled treatment of diseased tissue and the like existing in living beings.

Another object is to provide new compositions of matter which may be specifically employed to deliver and disposed medication within or adjacent to diseased tissue, such as malignancies and the like existing within living beings.

Another object is to provide an improved method for delivering small quantities of highly potent chemicals to diseased tissue, such as tumors and the like, for destroying such tissue.

Another object is to provide an improved method for delivering select amounts of chemicals useful in altering tissue cells at one or more select sites in a living being.

Another object is to provide a system and method for delivering diagnostic material, such as a dye or radioactive tracer to a disease site, such as a tumor, or a select body organ to permit visual or instrument inspection to be made, wherein said diagnostic material is released from encapsulation at the site and does therefore not affect tissue in other locations of the body.

Another object is to provide a system and method for delivering drugs including organic and inorganic medication and biological elements and tracer material to a selected site such as a concentration of a specific antigenic material within a living body using microcapsules made of biodegradeable material which degrades under the action of body fluid after a time sufficient to permit such microcapsules to become targeted to specific antigenic material or cells existing within a living body.

Another object is to provide improvements in drug units capable of delivering quantities of a biological or chemical drug to one or more locations within a living being, such as a disease or cancerous site, to the exclusion of other portions of the body and without releasing such drug in the bloodstream prior to their delivery to the selected location or site.

Another object is to provide improvements in drug units which may be targeted to selected locations or cells within a living being, such as cancer cells, and may be selectively and controllably released at such location or locations.

Another object is to provide an improved method for delivering a drug or medication to a select location within a living being, which method may be human-controlled as to the release of such drug or medication.

Another object is to provide improvements in the structures of drug units which may be employed to a selectively dispense chemical or biological agents within a living being.

Another object is to provide a method for selectively dispensing one or more drugs or chemcials at selected locations or against selected tissue or disease cells within a living being.

Another object is to provide a method for treating a disease, such as malignancy, by a combination of radiation and a drug which is selectively dispensed within a living being.

Another object is to provide a method of treating a malignancy or other disease by means of radiation and one or more chemical or biological agents released at the site of such malignancy by controlled radiation.

Another object is to provide a method of controllably dispensing a liquid material at a selected site within a living being, without the need to flow such liquid through a hollow needle or capillary.

Another object is to provide a method for remotely controlling the release of a drug from a reservoir or capsule located within a living being.

Another object is to provide a method for remotely controlling with radiation the release of a drug from a reservoir or reservoirs located within a living being.

Another object is to provide a method for explosively releasing a quantity of a drug or medication within a living being by destroying at least a portion of its container disposed within tissue of such living being.

Another object is to provide a method of detecting a location of a disease or disease site within a living being and controllably releasing a drug at such site immediately after such detection is made.

Another object is to provide improvements in the structures and operation of body implants for releasing drugs or the like within a living being.

SUMMARY OF THE INVENTION

In the invention as described herein is directed to compositions and a method for targeting and applying those compositions to selected locations within a living being. The compositions are for use in a drug delivery system and are adapted to be disposed adjacent select tissue in a living being for selectively treating that tissue.

A composition of the invention comprises a multitude of drug units each including respective drug containers and each defining at least one enclosed volume for containing a medicinal material. There is a small quantity of a selected medicinal material contained within the enclosed volume of the containers. The drug units include an activatable material for causing their respective drug containers to release their contents upon activation of the activatable material after each drug unit is disposed adjacent the select tissue being treated. Each drug unit is effective to permit the medicinal material it contains to be delivered directly to the select tissue without directly contacting or effecting body tissue and the like located distal from said select tissue.

In one composition of the invention, the activatable material comprises a quantity of a normally inactive nuclide material retained by each of the containers. The nuclide material becomes radioactive to effect the release of the medicinal material from the container when a beam of activating radiation is directed thereat from outside a body of a living being in which the containers are disposed. Various types of nuclides effectuate the opening of the container to release the medicinal material in various ways.

In another embodiment of the composition of matter, the activatable material comprises a biodegradable material which degrades after a time delay once the drug units have entered the body and moved to a select site for treating the tissue within the living being.

In another embodiment of the invention, each drug unit includes at least one antibody attached to the containers for targeting the drug unit to select antigenic material located within the body of a person to be treated by the medicinal material. Such antibody may comprise a monoclonal antibody that is targeted to a specific type of antigen associated with a specific cancer. The antibody may be bonded to the outer surface of the microcapsules of each of the drug units and is operable to attach the drug units to respective cancer cells by delivery thereto in the body fluid of a living being to whom the dose of the composition is administered.

The compositions of the present invention comprise a plurality of drug containing reservoirs employed either per se or in combination with each other. The reservoirs are either partially or completely destroyed, or a major portion thereof is radioactively destroyed or melted. Such partial or complete destruction may be effectuated by a nuclide disposed either within the material defining the container wall adjacent the wall of the container or in its contents. The nuclide is rendered radioactive by the application of external radiation. The radioactivity of the nuclide generates explosive nuclear energy or heat for disintegrating or melting a small thermoplastic valve or plug or a portion of a wall of a container. The nuclear energy or heat may also be used for effecting a chemical reaction resulting in the explosion or partial destruction of the container or the penetration of a portion of its wall to provide one or more openings therein.

The container or capsule is implanted, delivered by catheter or otherwise inserted into tissue, a bone, body cavity, or duct. The container may be delivered alone or in combination with a multitude of additional similar capsules each containing a normally inactive nuclide which may be rendered active to effect a miniature explosion to penetrate or destroy the fluid container or containers at the site of their use. The activation of the nuclide may also generate heat for melting a thermoplastic material forming a portion of the wall of such a container or defining a valve in a passsageway thereof so as to permit the thermoplastic material to flow or contract thereby providing an opening through which medicinal material may be released. The fluid medicinal material would thereby be delivered to adjacent tissues where it would be used for diagnostic or treatment purposes.

In a further embodiment of the invention, one or more amounts of a medication or a plurality of medications are combined with a polymer, protein or fat which forms part of the drug unit. The medication may be either attached to or encapsulated by such polymer, protein or fat. In a particular form, encapsulation is effected in the form of one or more microballoons or liposomes which form the major portion of the drug unit. Such encapsulating material becomes porous, ruptured or otherwise conditioned to release the incapsulated medicinal material when the nuclide of the drug unit is rendered radioactive.

A method of the invention effects a medical treatment or diagnosis at a selected location within the body of a living being. Each of a multitude of drug units contains a quantity of a drug encapsulated within the drug unit. A select quantity of the drug units is administered to the living being. A portion of the administered drug unit is allowed to travel to a location in the body to become disposed adjacent tissue to be treated with the encapsulated drug. The drug unit includes an encapsulating material which is maintained outside of the tissue being treated by the medicianal material is allowed to interact with the target cells aparts from the incapsulating material. Various methods of administering and causing the compositions of matter to move through the body of the living being are disclosed.

BRIEF DESCRIPTION OF DRAWINGS

With the above and such other objects in view as may hereinafter more fully appear, the invention consists of the novel combinations and arrangements of biological and chemical elements making up the drug units as exemplified by the structures shown in the drawings and the methods for apply same to living being, but is to be understood that changes, variations and modifications may be resorted to which fall within the scope of the invention as claimed.

FIG. 1 is a cross sectional view of a drug unit defined by a bulbous capsule containing one or more chemicals and one or more particles of a nuclide.

FIG. 2 is a cross-sectional view of the drug unit of FIG. 1 having a portion of its sidewall destroyed or ruptured when a particle or particles of a nuclide attached to its sidewall, is rendered radioactive and explodes against the sidewall.

FIG. 3 is a cross-sectional view of a spherically shaped drug unit and its contents.

FIG. 4 is a cross-sectional view of a drug unit which comprises a capsule containing a chemical or biological agent and one or more particles of a nuclide and an antibody, such as a monoclonal antibody, attached to a portion of the side wall of the capsule.

FIG. 5 is a cross-sectional view of a drug unit formed of a spherically shaped central body having a plurality of antibodies attached to its exterior surface.

FIG. 6 is a fragmentary view in partial cross-section of a portion of a container, such as a capsule, having a necked down portion containing one or more nuclide paritcles therein which may be rendered radioactive to render the necked down portion porous or to partially destroy same to permit the flow of contents from the container.

FIG. 7 is a fragmentary view in cross-section of a portion of a container having multiple cells containing a drug or drugs and means for selectively effecting the dispensing of the contents of each cell, and FIG. 8 is a fragmentary view in cross-section of a portion of a drug unit containing one or more particles of a nuclide which may be rendered radioactive with suitable radiation.

DETAILED DESCRIPTION

In FIG. 1, a drug unit 10 of the invention may comprise one of a multitude of such units disposed in a liquid or capsule which is administered to a living being. The drug unit 10 comprises a bulbous capsule 11, shown as having a spherical or ellipsoidal shape, although it may have any other suitable shape. A side wall 12 completely surrounds contents 15 which may comprise any suitable type of medication such as an organic or inorganic liquid chemical, a plurality of such chemicals, a biological material, such as an antibiotic or a liquid containing one or more living or dead virus, bacteria, antibodies, phages, or other material which is desired to be dispensed within or in the immediate vicinity of disease tissue or disease cells existing within a living being.

A small particle 14 is supported against a portion of the outside surface 13 of the wall 12. Particle 14 is a nuclide material, such as boron-10 or one of the nuclides described in my hereinabove setforth patent applications. Such particle 14 may comprise a plurality of particles bonded by a suitable resin or other material coating the outside surface 13 of capsule 11. Particle 14 may be rendered radioactive and caused to generate radiation or explode as illustrated in FIG. 2, to rupture a portion of the wall 12 to permit the contents 15 of capsule 11 to flow through the opening 12R. A plurality of openings may be formed in the wall when particles of such nuclide are simultaneously rendered radioactive. Such particle 14 may be so rendered radioactive when the drug unit 10 is disposed or flows to a select location within a living being, such as a location of diseased tissue, dead or calcified tissue or bone desired to be subjected to a chemical or biological agent, such as the contents 15 of the capsule 11.

The contents 15 may be under slight pressure during the formation of the capsule 11 or may be pressurized as the result of the heat or pressure of the radiation generated when the particle or particles 14 become radioactive. Accordingly, one or more of such particles may also be disposed within the body of the contents 15 or against the inside surface of the wall 12 or within such wall for such purpose and/or to render the wall 12 ruptured or porous to permit flow of the contents 15 from the capsule and/or absorption of body fluid into the capsule to mix or react with its contents.

The capsule 11 may vary in size from less than a thousandth of an inch in diameter to several thousandths of an inch in diameter or more, if a multitude of such capsules are utilized to deliver a chemical or biological agent to a particular location within a living being via the bloodstream or by direct injection to such location. It may also comprise a larger capsule which is injested by mouth, inserted by catheter or implanted by of surgery at a select location in tissue or a body duct. Wall 12 may be made of a synthetic polymer, such as a suitable plastic resin, a starch, protein, fat, cell tissue, a combination of such materials or other organic matter. It may be employed per se or in combination with other elements as described hereafter. Similar or differently shaped capsules of the types illustrated in the drawings may be combined or mixed and may contain a plurality of different elements or drugs mixed in each or provided in separate such elements or drugs cooperate in alleviating a malady such as by attacking or destroying bacteria or diseased tissue, improving the condition of living cells, changing the structure of living tissue or cells, dissolving or destroying tissue cells, repairing cells or cell damage, etc.

In FIG. 3, a drug unit 20 of the type shown in FIGS. 1 and 2, comprises a spherically shaped container or shell 21 of one or more of the materials described with a spherical sidewall 22. The outer surface 23 may contain one or more particles of a nuclide of the type described and/or one or more antibodies, such as monoclonal antibodies, attached thereto by a suitable resin or assembled with the container 21 by a suitable derivatizing agent.

Disposed within the hollow interior of spherically shaped container 21 is a liquid material or drug 25 having one or more particles 24 of a nuclide or a plurality of nuclides floating or supported therein. Such nuclide or nuclide particles 24 may be rendered radioactive, as in FIG. 2, by directing a beam or beams of neutrons at the drug unit 20, such a neutron beam source may be located outside the body in which the drug units are disposed. The neutrons render the one or more particles 24 radioactive in a manner to either explode or generate sufficient radiant energy to cause the liquid contents 24 to at least partially evaporate or otherwise expand in a manner to force such contents through the wall 22, which may be porous or rendered porous or may be ruptured by the internal pressure effected when the particle or particles 24 become radioactive.

In such a manner, the contents 25 may be completely or partially expelled from the container and applied to adjacent or ambient tissue or disease matter located within a human living being adjacent the drug unit 20. In a particular form of FIG. 3, one or more particles of a nuclide disposed on the outer surface 23 of the wall 22 may be rendered radioactive and explode to rupture a portion or portions of the wall, rendering same porous or providing an opening therein or destroying such wall so that the contents 25 may flow therefrom to surrounding material.

In FIG. 4 is shown a modified form of drug unit 30 formed of a capsule 31 of the type illustrated in FIGS. 1 and 2 or 3. A spherical or ellipsoidally shaped sidewall 31 completely surrounds a liquid, cream or solid drug or chemical 33 having one or more particles 34 of a nuclide or nuclides disposed therein for use as described above.

Bonded or otherwise attached to a portion of the exterior surface 32 of wall 31 is an antibody 36, such as a monoclonal antibody, which is targeted to a specific antigen located within a living being. Such antigen may comprise, for example, the surface of a cancer cell, bacteria, disease tissue or other material desired to be affected by the chemical or agent 33 released from the drug unit 30 when the nuclide particle or particles 34 located within the contents 33 or disposed within or against the surface 32 of the wall 31 of the capsule, are rendered radioactive and explode or generate sufficient heat or radiation to effect one or more of the described actions with respect to the wall 31 of the capsule, such as render same porous or ruptured. A polymer or other derivatizing agent 35 is employed to bond the antibody or monoclonal antibody 36 to a portion of the surface 32 of the capsule.

In FIG. 5 is shown a modified form of FIG. 4 wherein a drug unit 40 is composed of a base unit or container 41 which is illustrated as a porous spherical body, the cells 43 of which contain a drug or chemical dispensed therefrom to surrounding fluid or tissue. One or more particles 44 of a nuclide of the type described above, are disposed within the body of the spherical container 41 and/or against the outside surface thereof to be rendered radioactive when a beam or beams of radiation, such as neutrons, are directed thereat. The radiation is absorbed by the particle or particles to effect such radioactivity which may comprise explosive and/or nonexplosive radiation. Thus, liquid or particulate drug material (1) may be forced from the cells of the container 41, (2) effect a chemical reaction resulting in such action or (3) partially or completely destroy the container 41 to release its contents.

A plurality of antibodies 45 as disposed against and bonded to the outside surface 42 of the container 41. In this embodiment, monoclonal antibodies 45 are targeted to a particular antigen, such as a disease or cancer cell or other cell located within the body of a living being to be treated, destroyed or otherwise affected by the action of chemical or biological agent carried by the container 41 and, if so constructed, by the radioactivity generated when the nuclide particle or particles 44 are rendered radioactive as described.

In FIG. 6 is shown a container assembly 50, which may be a preformed capsule or otherwise shaped implant having a container body 51 with a suitable sidewall 52 and having contents 56, such as one of the chemicals or biological agents described above, which contents are desired to be dispensed from a neck portion 53 of the container. Supported within the neck portion 53 is a solid material 54 containing one or more particles 55 of a nuclide of the type described. When such particle or particles 55 are rendered radioactive by externally applied radiation, they may heat and melt the material 54 or explode and rupture such material and a portion of the neck 53 of the container. Thus, contents 56 flow from container 50, either by capillary action if the neck 53 is of a capillary construction, by internal pressure created by the heat of radiation or existing within the container, by gravity or osmosis effected when the wall 52 of the container and/or the filling material 54 is rendered porous or when porous filling material 54 is exposed to the exterior of the container when a portion of the neck wall 52 neck is ruptured or destroyed when a particle or particles 55 become radioactive.

In FIG. 7 is shown a portion of a container 60 having a sidewall 61 and a plurality of interior wall portions 65 extending completely through the container to provide a plurality of separate chambers 66. Each chambers 66 may contain different portions of the same chemical or biological agent or different chemicals or biological agents.

Disposed against select portions of the sidewalls 61 and either bonded to the exterior surface 62 of the container 60 or supported within a material 63 coating of such sidewall, are a plurality of particles 64 of a nuclide. In FIG. 7, one particle 64 is shown aligned with each chamber 66 of although a multiple of such particles may be so aligned and disposed.

When a beam or beams or radiation, such as neutrons, are selectively directed at selected portions of the sidewall 61 and the particle or particles 64 aligned therewith, the selected portions of the sidewall may be ruptured, rendered porous or have small openings formed therein when the particle or particles of nuclide are rendered active as described. Thus, contents 67 are selectively disposed when the sidewall portions of the chamber or chambers 66 are ruptured or rendered porous when the selected nuclide particle or particles become radioactive.

In FIG. 8 is shown another form of the invention a material 73, which may form a drug unit or a multitude of such drug units, a filament or larger capsule which is injected or injested into a living being or applied by means of a catheter to a selected portion of the body or a body duct of such living being. The material 70 may be solid through and through or formed with cells or pores containing a chemical or biological agent 72. The material 70 may also comprise a chemical or biological agent to be selectively dispensed at a select site within a living being for one or more of the purposes of destroying, modifying, or otherwise beneficially affecting tissue, cells or other material existing within a living being.

In addition to particles 72 of a chemical or biological agent within the material 71, a plurality or multitude of particles 74 of a nuclide are provided. Selected application particalizing of portions of the material 71 and its contents by the resulting miniature nuclear explosions or when the heat of such nuclear reactions is generated and causes material to be dispensed from the cells of solid material 71 or to melt small quantities of such material and/or its contents. The particles 74 may also be bonded to select portions of the exterior surface of material 71. When particles 74 are rendered radioactive as described select quantities of such material may be exploded or particalized and dispensed from the surface of the material into surrounding fluid or tissue for treating same as described above.

Nuclides will provide miniature explosive atomic reactions capable of rendering microcapsules such as liposomes, starch, protein or fat microballoons in the order of one to ten microns or greater in diameter porous or ruptured to release their liquid medication contents to surrounding tissue or cells, may include boron-10, cadmium-113, lithium-6, samarium-149, mercury-199, gadolinium-155 and gadolinium-157. Nuclides which may be attached or coated on or disposed within the described microcapsules for diagnostic and indicating purposes include such radioactive elements as cobalt 57; galium 67, cesium 131, iodine 131, iodine 125, thalium 201, technicium 99 m, indium 111, selenium 75, carbon 11, nitrogen 13 or a combination of such radioactive elements. In a particular form of the invention, both a neutron activated and atomically explosive particle or particles, such as atoms, of a nuclide and a normally radioactive nuclide of the groups above may be provided in a single drug unit per se or in combination with a chemical as described.

MODIFICATIONS OF THE STRUCTURES ILLUSTRATED IN THE DRAWINGS AND HEREINBEFORE DISCLOSED

The following modifications are noted which may be made to the drug units hereinbefore disclosed and illustrated in the drawings.

1. A plurality of microcapsules, microballoons, liposomes or otherwise structured containers may be attached together per se or in a larger container or capsule. Sucn containers may be made of the same or different chemicals, organisms or other organic material, bacteria or virus useful as a drug or medication for the treatment of a particular disease, malady or other condition in a living being or organism. The larger container or capsule may be attached to one or more antibodies, such as monoclonal antibodies targeted to a specific antigen, such as a specific cancer cell, organ or other matter existing within such living being. The container-/antibody combination may define one of a multitude of drug units which are administered by ingestion, injection, catheter or other means for the purpose of allowing a quantity thereof to target to specific site or sites, such as disease sites, tumors, an organ or organs, etc.

2. Each or one or more of the units of (1) or the microcapsules of the units may contain one or more particles of a nuclide operable to become radioactive and to explode or disintegrate. Thus, the contents of the microcapsules are released when adjacent the antigenic material to which the antibodies thereof are attached. The radioactive nuclides may generate radiation for otherwise effecting the release of such encapsulated material(s) as heretofore described.

3. Each or one or more of the capsules of (1) may also contain per se or in combination with one or more of the described chemicals or biological materials, a small quantity of a material useful in diagnosing and locating a malady, such as a tumor or tumors existing in a living being. This material may comprise a radioactive element or compound such as one containing a radionuclide or a dye. Such material may be released at the site of the tumor or cells to which the antibody become targeted, as decribed herein by activating the contained or attached nuclide with externally generated radiation directed through the body thereat. Release may also be effected when the container(s) biodegrade allowing the material to stain or radioactively indicate the location, shape and extent of the tumor, malignancy or otherwise diseased or malshaped malady.

4. The drug units may each be formed of one or more microballoons or microcapsules. The drug unit wall or walls are made of a biodegradable material, such as starch, a protein or a synthetic or organic polymer which dissolves or otherwise degrades to release the contents of the capsule(s). The material dissolves when subjected to the action of either the fluids of the body into which the drug units are injected or injested, or for a period of time sufficient to permit the drug units to become targeted, as described, to these specific antigens, such as cancer cells. Drug units may be made of biodegradable material which permits the medication carried by each unit to be substantially simultaneously released with that of the other units or to be time released by biodegradation at different time intervals so that treatment of tissue therewith and/or diagnosis therewith is sustained over a prolonged period of time.

5. A chemical or chemicals operable to dissolve or biodegrade the capsules of certain of the drug units may be carried by others of the drug units and released therefrom by the described nuclide activation means or biodegradation with body fluid to flow to others of the drug units and release their contents.

6. The drug units and their contents may be employed to block the flow of body fluid, such as blood in capillaries, arteries and veins or other body fluids in ducts through which they flow. A suitable flow blocking agent is released from the drug units as described herein by activating and atomically exploding a nuclide particle or particles and/or generating radiation such as heat operable to melt or condition the microcapsules to release their contents at the site where such agent is desired to be released. Such agent may comprise an organic or inorganic adhesive or coagulating chemical.

7. The chemical or biological agents contained by the described drug units may be selectively released, as described, to destroy restrictions within a living being or organism. These restrictions include coagulated blood or other matter, growths such as tumors or the like by chemical and/or biological activity resulting when such contents of the microcapsules are so released. The explosive effects of the activated nuclide particles may also be used per se and/or in combination with the effects of the anti-blocking, anticoagulating or dissolving chemical or chemicals released as described to alleviate or remove such a blockage.

8. A combination of chemical and/or biological activity and radioactivity, may also be employed to simultaneously and/or sequentially operate on tissue, such as a tumor or otherwise diseased tissue or bone by employing drug units of the type described which contain one or more particles of a normally inactive nuclide and a chemical or biological agent. Activation of the nuclide of the drug units as described may serve two purposes. One is to release the encapsulated chemical or biological agent by destroying or rendering porous the wall of the capsule as a result of the explosive effect of the radioactivity and/or the heat of radioactivity. The other is to destroy certain of the tissue cells such as cancer cells adjacent the drug units targeted thereto. When the capsule is destroyed or a hole is formed in its wall, the chemical and/or biological agent therein is released and may attack and destroy or otherwise treat the adjacent or targeted cells of cancer or diseased tissue.

9. The monoclonal antibody attached to the drug units may be targeted to certain virus or bacteria existing within the living being treated. The drug unit to which such antibody is attached, may be activated with external radiation such as neutrons which render one or more particles of a nuclide, such as boron-10, to explode and/or chemically or biologically attack such bacteria or virus when so targeted.

10. The drug units described may contain one or more biological agents, such as living or killed bacteria, virus, phages, antibiotic agents, antibodies, interferon or other agent which will attack or otherwise beneficially affect or treat a human malady when released from the microcapsules as described.

11. Two types of normally inactive radionuclides may be disposed within a single capsule. Alternatively, capsules of the same or different drug units may contain such different nuclides. One type nuclide explosively disintegrates upon being rendered radioactive with neutrons or other form of radiation as described. The other type nuclide is released from the capsule by the explosive action and is rendered radioactive in a non-explosive manner by the radiation generated by the other and/or the same or a different externally generated radiation applied thereto from outside the body of the patient being treated.

12. A biological agent, such as select bacteria, virus, phage or other organic matter capable of procreation or self-reproduction, may be disposed within and released as described from one or more of the targeted drug units. Upon release, the agent may reproduce rapidly at the site of their release for promoting or effecting a medical treatment of a disease or other malady. An additional or supplemental organic or inorganic material released from others of the capsules of a unit or other units of drug may be employed to be released, as desribed. Such additional material will promote or effect such multiplying or reproduction and/or supplement and improve the action of such reproducing living matter at the site of their release.

Antibodies, such as monoclonal antibodies, may be produced and bonded to the microcapsules, as disclosed in my said copending patent applications. Further reference is made to the following U.S. Patent for teachings as to the production of monoclonal antibodies: U.S. Pat. Nos. 4,434,230; 4,423,034; 4,381,295; 4,364,397 and 4,364,396.

13. Fine magnetic particles, such as micro-particles of a ferrite or magnetite on the order of a few microns in diameter or less may be incorporated into microcapsules of the types described herein. Such particles may be bonded to the surface of the microcapsules Smaller particles of such magnetic materials may be encapsulated within the capsules together with the described chemical or biological medication and the particle(s) or liquid defining the normally inactive nuclide(s). Such drug units may be employed per se or with other drug units having antibodies, such as monoclonal antibodies attached to their surfaces. Drug targeting is effected by magnetic manipulation and attraction per se or in combination with antibody-antigen targeting. A quantity of such magnetic drug units may be injected or otherwise introduced into the bloodstream of a patient and allowed to circulate in the circulatory system. A suitable permanent magnetic or electromagnet is located either outside the body in alignment with a tumor, infection or other localized malady or supported by the head of a catheter disposed near the tumor or infection to attract and retain the magnetic drug units at tumor or infection site. Thereafter the medication contained within the capsules of the drug units may be released, as described, by biodegradation of the capsule wall, by rendering the nuclide radioactive to dissolve or rupture the wall, by explosion of the capsule or by chemical action occurring when certain of the capsules biodegrade and release their chemical contents or when such capsules are ruptured or rendered porous with radioactivity.

14. In any of the embodiments described above, hormones or other biological agents which fight infection or attract body cells such as white blood cells may be incorporated into the capsules forming part of the drug units, to be released, as described, at one or more sites, such as tumors and infection sites existing in a living body.

In another form of the invention, drug units containing a plurality of different monoclonal antibodies may be formed with a radionuclide. The antibodies may form part of each unit or exist in separate drug units forming a dose thereof. Each different antibody is targeted to a different antigen such as different cancer cells or other disease defining antigenic matter or cells. The unit may include a radionculide which is normally radioactive and/or a nuclide such as boron-10 or the like which is not normally radioactive but is capable of being rendered radioactive at the site of the diseased or cancerous tissue or tumor. A dose of such units may be injected or injested into a living being with a number of maladies for detecting the sites of such number of maladies as described and/or treating the different diseases at such site or sites with radiation generated as described or by other means.

In yet another form of the invention, drug units of any of the types hereinbefore described may be disposed in a container capable of effecting timed or externally controlled release of select quantities of such units into the body or bloodstream of a living being. This makes it possible to periodically determine, as described, if a malady such as a cancer or cancers exist and/or to effect treatment thereof as described following the effecting of suitable detection and monitoring procedures. Such containers may comprise an implant, a plurality of implants or an injectin device worn against the skin. It may also comprise a biodegradable container or a plurality of biodegradable capsules injested or implanted in the body of the patient or subject being monitored and/or treated. If the antibodies of the drug units do not target such units to a disease site or cancer cells, they eventually are excreted from the body, a process which may also be monitored by the analysis of urine and feces of the person being monitored for diagnostic purposes.

I claim:
1. A method of effecting a medical treatment or diagnosis, said method comprising:
   (a) forming a multitude of drug units, each containing a quantity of a drug encapsulated by a carrier material within the drug unit formed,
   (b) administering a select quantity of said drug units to the body of a living being,
   (c) allowing at least a portion of said administered drug units to travel through the body to a select location in the body and to become disposed adjacent select tissue at said select location to allow said select tissue at said select location to be treated with the encapsulated drug thereof, and
   (d) after a substantial quantity of said drug units are so disposed, causing the drug contained in each unit to be released from the carrier material encapsulation and to flow to tissue adjacent which said units are disposed.

2. A method in accordance with claim 1 wherein the quantities of drug contained by said drug units are released by causing said encapsulating carrier material of said units to become ruptured to destroy the encapsulating effect.

3. A method in accordance with claim 1 wherein the quantities of drug contained by said drug units are released from encapsulation by causing said encapsulating carrier material of said drug units to become porous and release drug contained thereby.

4. A method in accordance with claim 1 wherein the quantities of drug contained by said drug units are released from the drug units by causing said encapsulating carrier material of said drug units to dissolve or biodegrade in body fluid.

5. A method in accordance with claim 1 wherein the quantities of drug contained by said drug units are released from the drug units by causing said encapsulating carrier material of said units to biodegrade within said living being at a select time after being administered to the body of said living being.

6. A method in accordance with claim 1 wherein the quantities of said drug contained by said drug units are released therefrom by causing a quantity of a nuclide contained in at least certain of said units to become radioactive and, in so becoming, to explosively destroy at least a portion of the encapsulating carrier material to release the encapsulated drug from the units.

7. A method in accordance with claim 1 wherein a substantial portion of said administered drug units are permitted to travel in the bloodstream of said living being and to flow with the blood of said living being to the tissue of the body to be treated when the drug encapsulated in said drug units is released from encapsulation by said drug units at the site of said tissue.

8. A method in accordance with claim 7 wherein said drug units each are formed of at least one microcapsule encapsulating a quantity of said drug, and the targeting of said drug units to the site of said tissue is effected by respective antibodies attached to said drug units, and said antibodies operatively attach to antigens located at said select body site of said tissue.

9. A composition of matter for use in the treatment of a malady of a living being, said composition comprising:
(a) a medical treatment dose defined by a multitude of drug units,
(b) each drug unit including a microcapsule made of a degradable material which biodegrades in the presence of a body fluid and which may be administered to a living being to expose the microcapsules of such dose to body fluid as the drug units travel through the body to a select site within the body,
(c) a small quantity of a drug useful in the treatment of said malady by reacting with tissue of the body at said select site and contained within each of said microcapsules,
(d) at least one biologically engineered, targeting monoclonal antibody, targeted to a specific type of antigen associated with a specific cancer,
(e) said antibody being bonded to an outer surface of said microcapsules and operable to attach the drug units to respective cancer cells by travelling through the body fluid of a living being to whom said dose is administered,
(f) said biodegradable material being operable in the presence of the body fluid to degrade and release the drug contents of said microcapsules after a time delay once said drug units have entered the body and said drug units are targeted to a select cancer site in the body of the living being to whom said medical dose has been administered.

10. A composition of matter for use in a drug delivery system and adapted to be disposed adjacent select tissue in a living being for selectively treating said tissue, said composition comprising:
(a) a multitude of drug units each including respective drug containers and each defining at least one enclosed volume for containing a medicinal material,
(b) a small quantity of select medicinal material contained within the enclosed volumes of said containers, and
(c) said drug units including an activatable material for causing their respective drug containers to release their contents upon activation of said activatable material after each drug unit is disposed adjacent select tissue within a living being,
(d) each of said drug units being effective to permit the medicinal material it contains to be delivered directly to said select tissue without directly affecting body tissue located distal from said select tissue,
(e) said activatable material comprising a quantity of a normally inactive nuclide material retained by each of said containers,
(f) said nuclide material being operable to become radioactive to release the medicinal material from the container when a beam of activating radiation is directed thereat from outside a body of a living being in which said containers are disposed.

11. A composition of matter in accordance with claim 10 wherein
each quantity of nuclide material retained by each container is operable to become explosively radioactive of an intensity such that, when activated with a beam of activating radiation, it explosively forms an opening in the wall of the container for releasing said medicinal material.

12. A composition of matter in accordance with claim 11 wherein
said nuclide material is selected from the group including boron 10, cadmium-113, samarium-149, mercury-199, lithium-6, gadolilinium-155 and gadolium-157.

13. A composition of matter in accordance with claim 10 wherein
each quantity of said nuclide material is operable to become explosively radioactive, when activated, to rupture the wall of the container and to thereby effect the release of said medicinal material from said container.

14. A composition of matter in accordance with claim 10 wherein
said nuclide material is provided as particles bonded to the outside surface of said containers.

15. A composition of matter in accordance with claim 10 wherein
each enclosed volume is defined by walls of said containers, and
said nuclide material is provided as particles encapsulated within the walls of said containers.

16. A composition of matter in accordance with claim 10 wherein
said nuclide material is provided as particles contained within a cell of each of said containers.

17. A composition of matter in accordance with claim 10 wherein
said nuclide material is provided as particles of a nuclide mixed with the drug contained in each of said containers.

18. A composition of matter in accordance with claim 10 wherein
each drug unit includes at least one antibody attached to said containers for targeting the drug unit to a specific antigen of a specific cancer cell existing within the body of a living being to be treated by said composition of matter.

19. A composition of matter in accordance with claim 10 wherein
each drug unit includes at least one antibody bonded to said containers,
said antibody being targeted to select antigenic material located within the body of a person to be treated by said medicinal material.

20. A composition of matter in accordance with claim 10 wherein
said container is made of a heat meltable material,
said nuclide material, upon becoming radioactive, generates heat sufficient to melt the material of the wall of said container thereby releasing the medicinal material.

21. A composition of matter in accordance with claim 10 wherein
said nuclide material, upon becoming radioactive, generates heat sufficient to pressurize the drug contents of each container to force the medicinal material from the containers.

22. A composition of matter in accordance with claim 21 wherein
the medicinal material contained within each of said containers is in a liquid state, and
the heat generated, when the nuclide material thereof is rendered radioactive, is sufficient to heat the contents of each container a sufficient amount to expand same and to burst the wall of the container and release the medicinal material therefrom.

23. A composition of matter in accordance with claim 10 wherein
each of said medicinal material containers contains a plurality of particles of said nuclide material.

24. A composition of matter in accordance with claim 10 wherein
each of said containers is formed with a plurality of cells for encapsulating medicinal material therein.

25. A composition of matter for use in a drug delivery system and adapted to be disposed adjacent select tissue in a living being for selectively treating said tissue, said composition comprising:
(a) a multitude of drug units each including respective drug containers and each defining at least one enclosed volume for containing a medicinal material,
(b) a small quantity of a select medicinal material contained within the enclosed volumes of said containers,
(c) said drug units including an activatable material for causing their respective drug containers to release their contents upon activation of said activatable material after each drug unit is disposed adjacent select tissue within a living being,
(d) each of said drug units being operable to target the medicinal material it contains to permit it to be delivered directly to select tissue without directly contacting or affecting body tissue located distal from select tissue,
(e) said activatable material comprising a biodegradable material used to form the containers enclosing the medicinal material therein,
(f) said biodegradable material being operable to degrade in the presence of a body fluid to release the medicinal material contained by the container for uptake by the select tissue of the body of a living being in which said containers are disposed.

26. A composition of matter in accordance with claim 25 wherein
at least some of said containers contain at least one biological material such as a virus or bacterium, phage or antibiotic capable of effecting medical treatment when released therefrom.

27. A composition of matter for use in a drug delivery system and adapted to be disposed adjacent select tissue in a living being for selectively treating said tissue, said composition comprising:
(a) a multitude of drug units each including a respective drug container and each defining at least one enclosed volume for containing a medicinal material,
(b) a small quantity of a select medicinal material contained within the enclosed volumes of said containers,
(c) said drug units including an activatable material for causing their respective drug containers to release their contents upon activation of said activatable material after each drug unit is disposed adjacent select tissue within a living being,
(d) each of said drug units being effective to permit the medicinal material it contains to be delivered directly to select tissue without directly contacting or affecting body tissue located distal from said select tissue, and
(e) targeting material defined by at least one targeting unit targeted to a specific type of antigen associated with a specific cancer,
(f) said targeting material being bonded to an outer surface of the drug containers and operable to attach the drug units to respective cancer cells by travelling through the body fluid of a living being in which said containers are disposed.

28. A composition of matter in accordance with claim 25 wherein
the medicinal material is taken up by said body tissue without substantial uptake of the biodegradable material.

* * * * *